United States Patent [19]

Bernstein et al.

[11] 4,002,745

[45] Jan. 11, 1977

[54] COMPLEMENT INHIBITORS

[75] Inventors: Seymour Bernstein; Milton David Heller, both of New City, N.Y.; Joseph Peter Joseph, Cliffside Park, N.J.

[73] Assignee: American Cyanamid Company, Stamford, Conn.

[22] Filed: Nov. 18, 1975

[21] Appl. No.: 632,932

[52] U.S. Cl. .............................. 424/230; 424/234
[51] Int. Cl.² .................. A61K 31/61; A61K 31/60
[58] Field of Search ........... 424/331, 317, 230, 234

[56] References Cited

OTHER PUBLICATIONS

Arikawa et al.–Chem. Abst. vol. 57 (1962) p. 6603i.

*Primary Examiner*—Sam Rosen
*Attorney, Agent, or Firm*—Jack W. Richards

[57] ABSTRACT

Formaurin dicarboxylic acid and certain of its derivatives and salts thereof useful as complement inhibitors.

15 Claims, No Drawings

COMPLEMENT INHIBITORS

BACKGROUND OF THE INVENTION

The present invention resides in the concept of formaurin dicarboxylic acid, certain of its derivatives and salts thereof and their use as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. The standard reference for nomenclature of complement is *Bull. World Health Org.*, 39, 935–938 (1968). A more detailed discussion of the complement system and its role in body processes can be found in, for example, *Scientific American*, 229, (No. 5), 54–66 (1973); *Medical World News*, October 11, 1974, pp. 53–58; 64–66; *Harvey Lectures*, 66, 75–104 (1972); *The New England Journal of Medicine*, 287, 489–495, 545–549, 592–596, 642–646 (1972); *The Johns Hopkins Med. J.*, 128, 57–74 (1971); and *Federation Proceedings*, 32, 134–137 (1973).

The complement system can be considered to consist of three subsystems: (1) a recognition unit (C1q) which enables it to combine with antibody molecules that have detected a foreign invader; (2) an activation unit, (C1r, C1s, C2, C4, C3) which prepares a site on the neighboring membrane; and (3) an attack unit (C6, C7, C8, C9) which creates a "hole" in the membrane. The membrane attack unit is nonspecific, it destroys invaders only because it is generated in their neighborhood in order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragment and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diptheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review of Biochemistry*, 38, 389 (1969).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)]benzenesulfonic acid tetrasodium salt (chlorazol fast pink), heparin and a sulphated dextran have been reported to have an anticomplementary effect, *British Journal of Experimental Pathology* 33, 327–339 (1952). The compound 8,8'-{ureylenebis[m-phenylenecarbonylimino(4-methyl-m-phenylenecarbonylimino)]}di-1,3,5-naphthalenetrisulfonic acid, hexasodium salt (Suramin Sodium) is described as a competitive inhibitor of the complement system, *Clin. Exp. Immunol.*, 10, 127–138 (1972). German Pat. No. 2,254,893 or South African Patent No. 727923 discloses certain 1-(diphenylmethyl)-4-(3-phenylallyl)-piperazines useful as complement inhibitors. Other chemical compounds having complement inhibiting activity are disclosed in, for example, *Journal of Medicinal Chemistry*, 12, 415–419, 902–905, 1049–1052, 1053–1056 (1969); *Canadian Journal of Biochemistry*, 47, 547–552 (1969); *The Journal of Immunology*, 93, 629–640 (1964); *The Journal of Immunology*, 104, 279–288 (1970); *The Journal of Immunology*, 106, 241–245 (1971); and *The Journal of Immunology*, 111, 1061-1066 (1973).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808–812 (1972); *Allergol, Et. Immunopath*, II, 163–168 (1974); and *J. Allergy Clin. Immunol.*, 53, No. 5, 298–302 (1974).

SUMMARY OF THE INVENTION

It has now been discovered that certain formaurins interact with the complement reaction sequence, thereby inhibiting complement activity in body fluids.

This invention is particularly concerned with formaurin dicarboxylic acid, all pharmaceutically acceptable formaurin dicarboxylic acid derivatives and salts of both the acid and derivatives thereof having complement inhibiting activity. Representative formaurins within the scope of the present invention, include, for example: formaurin dicarboxylic acid; ammonium salt of formaurin dicarboxylic acid; sodium salt of formaurin dicarboxylic acid; potassium salt of formaurin dicarboxylic acid; methyl ester of formaurin dicarboxylic acid; ethyl ester of formaurin dicarboxylic acid; pentyl ester of formaurin dicarboxylic acid; acetylated methyl ester of formaurin dicarboxylic acid; methyl ether derivative of methyl ester of formaurin dicarboxylic acid; acetylated formaurin dicarboxylic acid; sodium salt of acetylated formaurin dicarboxylic acid; and methyl ether of formaurin dicarboxylic acid. Operable pharmaceutically acceptable salts of formaurin dicarboxylic acid and certain of its derivatives encompassed within this invention include alkali metal salts, alkaline earth metal salts, ammonium and substituted ammonias, e.g. diethanolamine, ethylenediamine, glucamino, trialkylammonium (e.g., ($C_1$–$C_6$ alkyl), pyridinium, etc. The preferred derivatives of this invention are the ($C_1$–$C_5$) acylates and ($C_1$–$C_5$) alkyl esters of formaurin dicarboxylic acid. The preferred salts are the ammonium and alkali metal salts of both formaurin dicarboxylic acid and the acylated derivatives thereof.

Formaurin dicarboxylic acid may be prepared as first disclosed by Kahl, L., *Chem. Ber.*, 31, 143 (1898) or according to the method of Smith, W. H., Sager, E. E. and Siewere, I. J., *Anal. Chem.*, 21, 1334 (1949). Acylation of formaurin dicarboxylic acid in the presence of pyridine provide the acylates of the invention. Treatment with diazomethane provides the methyl ether methyl ester of formaurin dicarboxylic acid. The salts of the free acid and acylates may be obtained by treatment thereof with a suitable base in aqueous alcohol.

This invention is concerned with a method of inhibiting the complement system in a body fluid, such as blood serum, which comprises subjecting body fluid complement to the action of an effective complement inhibiting amount of formaurin dicarboxylic acid, certain of its derivatives and salts thereof. The method of use of this invention is concerned with a method of inhibiting the complement system in a warm-blooded animal which comprises internally administering to said animal an effective complement inhibiting amount of formaurin dicarboxylic acid, certain of its derivatives and salts thereof. Body fluid can include blood, plasma, serum, synovial fluid, cerebrospinal fluid, or pathological accumulations of fluid such as pleural effusion, etc.

The formaurin dicarboxylic acid and certain of its derivatives and salts thereof of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. Formaurin dicarboxylic acid, its derivatives and salts herein may also be used in the therapeutic treatment of warm-blooded animals having non-immunologic diseases such as paroxysmal nocturnal hemoglobinuria, hereditary angioneurotic edema (such as Suramin Sodium etc.,) and inflammatory states induced by the action of bacterial or lysosomal enzymes on the appropriate complement components as for example, inflammation following coronary occlusion. They may also be useful in the treatment of transplant rejection.

DETAILED DESCRIPTION OF THE INVENTION

The following examples describe in detail the preparation and formulation of representative compounds of the present invention.

EXAMPLE 1

Methyl Ester of Formaurin Dicarboxylic Acid

A mixture of 15.2 g of methyl salicylate, 1.5 g of paraformaldehyde and 20 ml of acetic acid is heated to 100° C with stirring, then a solution of one ml of concentrated sulfuric acid in 3 ml of acetic acid is added with continued stirring for 5 minutes. The resultant mixture is then poured into ice water and is made alkaline by addition of solid sodium bicarbonate. The mixture is then extracted with benzene. The extract is dried over sodium sulfate and is treated with activated charcoal then the benzene is removed in vacuo. The residue is placed in a distillation apparatus with a 6 inch column. The bath temperature is raised to 158° C and several ml of liquid presumed to be methyl salicylate is collected at a distillation temperature of 94°–98° C/4.5 mm. The bath temperature is raised to 275° C and a further small fraction of distillate is collected at a distillation temperature of 211°–214° C/0.3 mm. This material solidifies on standing. The residue remaining is then distilled from a very small hold-back column at a bath temperature of from 250°–275° C and a distillation temperature of 204°–216° C/0.09–0.2 mm. The distillate is twice recrystallized from benzene to give 1.67 of the methyl ester.

To a 250 ml beaker containing 14 ml of concentrated sulfuric acid, cooled to 0°–5° C, is added portionwise with stirring 2.3 g of powdered sodium nitrite at such a rate as to keep the temperature from rising above 10° C, thus preventing evolution of red fumes. The solution is again maintained at 0°–5° C and 5.0 g of the methyl ester of 5,5′-methylenedisalicylic acid (prepared as above) is added portionwise with stirring, at such a rate as to keep the temperature below 5° C. Stirring is continued for one hour at 0°–5° C, then a second portion of the cold sodium nitrite in sulfuric acid solution (prepared as above) is added and stirring of the mixture is continued for one additional hour at 5° C. This mixture is allowed to come to room temperature overnight, then is poured into one liter of ice-cold distilled water. The solid is collected, then is resuspended in distilled water and is filtered and air-dried. The residue is dissolved in ethyl acetate, is dried over sodium sulfate and is filtered. The filtrate is evaporated in vacuo resulting in 5.3 g of a solid.

A chromatographic purification column is prepared with 240 g of thin layer chromatography grade silica gel. A 3.0 g portion of the product above is placed on the column and is eluted with approximately 200 ml of (60:40) ethyl acetate:hexane. The eluate is evaporated and the resulting glass is dissolved in 50 ml of ethyl acetate. A 5.0 g portion of silica gel powder is added and the mixture is evaporated, then it is added to a second column containing 100 g of thin layer chromotography grade silica gel. This column is eluted with approximately 100 ml of the (60:40) ethyl acetate:hexane mixture. The eluate is evaporated and then dried overnight in vacuo over phosphorus pentoxide to give the methyl ester of formaurin dicarboxylic acid.

EXAMPLE 2

Acetylated Methyl Ester of Formaurin Dicarboxylic Acid

A 200 mg portion of the methyl ester of formaurin dicarboxylic acid is dissolved in 0.5 ml of pyridine then 0.25 ml of glacial acetic acid is added and the solution is allowed to stand at room temperature over night. The material is poured into distilled water, the solid is collected, washed with water and dried in vacuo. The dried product is then dissolved in methylene chloride, is filtered through a hydrous magnesium silicate pad and is evaporated in vacuo to give the acetylated methyl ester of formaurin dicarboxylic acid.

EXAMPLE 3

Methyl Ether of Methyl Ester of Formaurin Dicarboxylic Acid

To a separatory funnel immersed in an ice-bath is added approximately 30 ml of a 50% aqueous solution of potassium hydroxide and 60 ml of methylene chloride. To this funnel is added portionwise 6.0 g of N-methyl-N-nitroso-N'-nitroguanidine, with swirling after each addition. After the addition is complete (15 minutes to ½ hour) the yellow solution of diazomethane in methylene chloride is allowed to remain in the ice-bath for approximately ½ hour longer. Then the aqueous layer is removed and the methylene chloride layer is added to cold sodium hydroxide pellets, to dry for ½ hour. The diazomethane reaction solution is then decanted and separated into 3 equal portions and kept at about 5° C until used.

A 250 mg portion of formaurin dicarboxylic acid is dissolved in 4 ml of methyl alcohol, then ⅓ of the diazomethane solution prepared above is added carefully. There is an immediate reaction with gas evolution and the red solution fades to a medium yellow color on standing. The solution is allowed to remain at room temperature for 18 hours, then air is bubbled in until dryness. The dried material is dissolved in methylene chloride and is filtered through a hydrous magnesium silicate pad. The solvent is evaporated in vacuo to give the methyl ether of the methyl ester of formaurin dicarboxylic acid.

EXAMPLE 4

Acetylated Formaurin Dicarboxylic Acid

A 500 mg portion of formaurin dicarboxylic acid is dissolved in 5 ml of pyridine, then 2.5 ml of acetic anhydride is added. The solution which lightens on the addition of acetic anhydride is allowed to remain at room temperature for 6 hours, then is poured into ice-cold distilled water. The clear solution is acidified with 2N hydrochloric acid and a pink precipitate forms. The precipitate is collected and washed with distilled water and is dried in vacuo. This material is dissolved in ethyl acetate and is dried over sodium sulfate. Then it is filtered and evaporated in vacuo to give the acetylated formaurin dicarboxylic acid.

EXAMPLE 5

Methyl Ether of Formaurin Dicarboxylic Acid

A 62 mg portion of the methyl ether derivative of the methyl ester of formaurin dicarboxylic acid is suspended in 4 ml of 2N sodium hydroxide. The suspension is heated on the steam bath for one and a half hours then is filtered to remove a trace of insoluble material. The solution is cooled and 2N hydrochloric acid is added until a solid is separated. The precipitate is collected by filtration, is washed with water and is dried in vacuo over phosphorus pentoxide at room temperature to give the methyl ether of formaurin dicarboxylic acid.

EXAMPLE 6

Sodium Salt of Acetate of Formaurin Dicarboxylic Acid

Treatment of the acetate of formaurin dicarboxylic acid with sodium carbonate in aqueous methyl alcohol gives the sodium salt.

EXAMPLE 7

Sodium Salt of Formaurin Dicarboxylic Acid

Treatment of formaurin dicarboxylic acid with sodium carbonate in aqueous methyl alcohol gives the sodium salt.

EXAMPLE 8

| Preparation of Compressed Tablet | |
|---|---|
| Ingredient | mg/Tablet |
| Formaurin Dicarboxylic Acid | 0.5–500 |
| Dibasic Calcium Phosphate N.F. | qs. |
| Starch USP | 40 |
| Modified Starch | 10 |
| Magnesium Stearate USP | 1–5 |

EXAMPLE 9

| Preparation of Compressed Tablet | |
|---|---|
| Ingredient | mg/Tablet |
| Acetylated Formaurin Dicarboxylic Acid | 0.5–500 |
| Dibasic Calcium Phosphate N.F. | qs. |
| Starch USP | 40 |
| Modified Starch | 10 |
| Magnesium Stearate USP | 1–5 |

EXAMPLE 10

| Preparation of Compressed Tablet - Substained Action | |
|---|---|
| Ingredient | mg/Tablet |
| Formaurin Dicarboxylic Acid | 0.5–500 as acid equivalent |
| Dibasic Calcium Phosphate N.F. | qs. |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 11

| Preparation of Hard Shell Capsule | |
|---|---|
| Ingredient | mg/Capsule |
| Formaurin Dicarboxylic Acid | 0.5–500 |
| Lactose, Spray Dried | qs. |
| Magnesium Stearate | 1–10 |

EXAMPLE 12

| Preparation of Oral Liquid (Syrup) | |
|---|---|
| Ingredient | % W/V |
| Formaurin Dicarboxylic Acid | 0.05–5 |
| Liquid Sucrose (70%) | |
| Methyl Paraben USP | 0.18 |
| Propyl Paraben USP | 0.02 |
| Flavoring Agent | qs. |
| Purified Water qs ad | 100.0 |

EXAMPLE 13

| Preparation of Oral Liquid (Elixir) | |
|---|---|
| Ingredients | % W/V |
| Formaurin Dicarboxylic Acid | 0.05–5 |
| Alcohol USP | |
| Glycerin USP | 45.0 |
| Flavoring Agent | qs. |
| Purified Water qs ad | 100.0 |

EXAMPLE 14

| Preparation of Oral Suspension (Syrup) | |
|---|---|
| Ingredients | % W/V |
| Formaurin Dicarboxylic Acid* | 0.05–5 (acid equivalent) |
| Polysorbate 80 USP | |
| Magnesium Aluminum Silicate, Colloidal | 0.3 |
| Flavoring Agent | qs. |
| Methyl Paraben USP | 0.18 |
| Propyl Paraben USP | 0.02 |
| Liquid Sucrose (70%) | 75.0 |
| Purified Water qs ad | 100.0 |

*As aluminum lake, micronized

EXAMPLE 15

| Preparation of Injectable Solution | |
|---|---|
| Ingredient | % W/V |
| Acetylated Formaurin Dicarboxylic Acid | 0.05–5 |
| Benzyl Alcohol N.F. | |
| Water for Injection qs ad | 100.0 |

EXAMPLE 16

| Preparation of Injectable Oil | |
|---|---|
| Ingredients | % W/V |
| Acetylated Formaurin Dicarboxylic Acid | 0.05–5 |
| Benzyl Alcohol N.F. | |
| Sesame Oil qs ad | 100.0 |

EXAMPLE 17

| Preparation of Injectable Depo Suspension | |
|---|---|
| Ingredient | % W/V |
| Formaurin Dicarboxylic Acid as Aluminum Lake Micronized | 0.05–5 (acid equivalent) |
| Polysorbate 80 USP | |
| Polyethylene Glycol 4000 USP | 3.0 |
| Sodium Chloride USP | 0.8 |
| Benzyl Alcohol N.F. | 0.9 |
| Hydrochloric acid to pH 6.8 | qs. |
| Water for Injection qs ad | 100.0 |

EXAMPLE 18

| Intra-Articular Preparation | |
|---|---|
| Ingredient | % W/V |
| Acetylated Methyl Ester Formaurin Dicarboxylic Acid | 2–20 |
| Sodium chloride (physiological saline) | |
| Benzyl Alcohol | 0.9 |
| *Sodium Carboxymethylcellulose | 0.75 |
| Polysorbate 80 | 0.04 |
| pH adjusted to 5.0–7.5 | |
| Water for Injection qs to | 100.0 |

*Sterile fill in individual vials under nitrogen. Forms a suspension.

EXAMPLE 19

| Intra-Articular Preparation | |
|---|---|
| Ingredient | % W/V |
| Acetylated Formaurin Dicarboxylic (Micronized) | 2–20 |
| Sodium Chloride (physiological saline) | |
| Benzyl alcohol | 0.9 |
| *Sodium carboxymethylcellulose (NaCMe) | –5 |
| pH adjusted to 5.0–7.5 | |
| Water for Injection qs ad | |

*Increasing the NaCMe forms a syrupy solution of water soluble compounds.

Formaurin dicarboxylic acid and its derivatives thereof, which are the essence of this invention, may be administered internally, e.g., orally or parenterally, such as in intraarticularly to a warm-blooded animal to inhibit complement in the body fluid of the animal, such inhibition being useful in the amelioration or prevention of those reactions dependent upon the function of complement, such inflammatory process and cell membrane damage induced by antigen-antibody complexes. A range of doses may be employed depending on the mode of administration, the condition being treated and the particular formaurin dicarboxylic acid or derivative being used. For example, for intravenous or subcutaneous use from about 5 to about 50 mg/kg/day, or every six hours for more rapidly excreted salts, may be used. For intraarticular use for large joints, such as the knee, from about 2 to about 20 mg/joint per week may be used, with proportionally smaller doses for smaller joints. The dosage range is to be adjusted to provide optimum therapeutic response in the warm-blooded animal being treated. In general, the amount of formaurin dicarboxylic acid or derivative administered can vary over a wide range to provide from about 5 mg/kg to about 100 mg/kg of body weight of animal per day. The usual daily dosage for a 70 kg subject may vary from about 350 mg to about 3.5 g. Unit doses of the salt can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tableting ingredients such as a corn starch, lactose, sucrose. sorbitol, talc, stearic acid, magnesium stearate, dicalcium phosphate, gums, or similar materials as non-toxic pharmaceutically acceptable diluents or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor). This test measures the ability of activated human C1 to destroy fluid phase human C2 in the presence of C4 and appropriate dilutions of the test compound. An active inhibitor protects C2 from C1 and C4; (ii) Test, Code 035 (C3– C9 inhibitor) — This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported unless otherwise stated; (v) Forssman Shock Test — Lethal shock is produced in guinea pigs by an i.v. injection of anti-Forssman antiserum and the harmonic mean death of treated guinea pigs is compared with that of simultaneous controls; (vi) Complement Level Reduction Test — In this test, the above dosed guinea pigs, or others are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparsion with simultaneous controls. The results appear in Table I together with results of test, code 026, 035, 036, Cap. 50, % inhibition and Forssman shock. Table I shows that the compounds of the invention possess highly significant in situ and in vivo, complement inhibiting activity in warm-blooded animals.

TABLE I

| Compound | In Vitro Activity | | | Cap 50* | In Vivo Activity Guinea Pig | |
|---|---|---|---|---|---|---|
| | Cl 026* | C-Late 035* | Shunt Inhib. 036* | mcg/ml | Forssman Vasculitis | % Complement Reduction |
| Formaurin Dicarboxylic Acid | 8, 7** | 3 | 4 | 111 | 77, 77 | 96, 94 |
| Acetylated Formaurin Dicarboxylic Acid | 1 | 1 | 4 | | | |
| Methyl Ether of Formaurin Dicarboxylic Acid | Neg | 1 | 5 | | | |

*Code designation for tests employed and referred to herein.
**Numbers represent the number of wells showing activity in a two-fold serial dilution assay. The higher the number the higher the activity.

We claim:

1. A method of inhibiting the complement system in a warm-blooded animal in need of such therapy which comprises internally administering to said animal an effective complement inhibiting amount of a pharmaceutically acceptable compound selected from the group consisting of formaurin dicarboxylic acid, $C_1$–$C_5$ acylate thereof, $C_1$–$C_5$ alkyl ether thereof, $C_1$–$C_5$ alkyl ester thereof, $C_1$–$C_5$ acylate of the $C_1$–$C_5$ alkyl ester thereof, $C_1$–$C_5$ alkyl ether of the $C_1$–$C_5$ alkyl ester thereof and salts thereof.

2. A method according to claim 1 wherein the derivative is the $C_1$–$C_5$ acylate of formaurin dicarboxylic acid.

3. A method according to claim 1 wherein the derivative is the $C_1$–$C_5$ alkyl ether of formaurin dicarboxylic acid.

4. A method according to claim 1 wherein the derivative is the $C_1$–$C_5$ alkyl ester of formaurin dicarboxylic acid.

5. A method according to claim 1 wherein the derivative is the $C_1$–$C_5$ acylated $C_1$–$C_5$ alkyl ester of formaurin dicarboxylic acid.

6. A method according to claim 1 wherein the derivative is the $C_1$–$C_5$ alkyl ether of the $C_1$–$C_5$ alkyl ester of formaurin dicarboxylic acid.

7. A method according to claim 1 wherein the salt is the alkali metal salt of formaurin dicarboxylic acid.

8. A method according to claim 1 wherein the salt is the alkali metal salt of the $C_1$–$C_5$ acylate of formaurin dicarboxylic acid.

9. A method according to claim 1 wherein the compound is administered intra-articularly.

10. A method according to claim 1 wherein the compound is formaurin dicarboxylic acid.

11. A method according to claim 2 wherein the derivative is acetylated formaurin dicarboxylic acid.

12. A method according to claim 3 wherein the derivative is the methyl ether of formaurin dicarboxylic acid.

13. A method according to claim 4 wherein the derivative is the methyl ester of formaurin dicarboxylic acid.

14. A method according to claim 5 wherein the derivative is the acetylated methyl ester of formaurin dicarboxylic acid.

15. A method according to claim 6 wherein the derivative is the methyl ether of methyl ester of formaurin dicarboxylic acid.

* * * * *